United States Patent [19]

Meneghin

[11] Patent Number: 4,628,087

[45] Date of Patent: Dec. 9, 1986

[54] PROCESS FOR THE PREPARATION OF PHARMACOLOGICALLY ACTIVE COMPOUNDS CONTAINING A SULFOXIDE GROUP

[75] Inventor: Mariano Meneghin, Revine-Lago, Italy

[73] Assignee: Zambon S.p.A., Vicenza, Italy

[21] Appl. No.: 607,562

[22] Filed: May 7, 1984

[30] Foreign Application Priority Data

May 13, 1983 [IT] Italy ................................ 21073 A/83

[51] Int. Cl.$^4$ ................... C07D 279/24; C07C 147/14
[52] U.S. Cl. ........................................ 544/41; 544/44; 544/42; 546/150; 548/331; 548/361; 549/393; 562/428; 564/101; 568/27
[58] Field of Search ..................... 568/27, 38; 562/428; 210/756; 544/41, 42, 44; 548/331, 361; 564/101; 549/393; 546/150

[56] References Cited

U.S. PATENT DOCUMENTS 2,793,234  5/1957  Metivier ............................ 568/27 X
3,006,963  10/1961  Buc et al. ........................... 568/27 X
3,465,044  9/1969  Hirano et al. ......................... 568/27
3,759,987  9/1973  Conn et al. .......................... 562/428

FOREIGN PATENT DOCUMENTS 0112960  6/1984  Japan ..................................... 568/27

OTHER PUBLICATIONS

Chemical Abstracts, vol. 91, No. 19, Nov. 5, 1979, p. 598, No. 157270q, Columbus, Ohio, USA, and JP-A 79 44612 (Asahi Chemical Industry Co., Ltd.) 09-04-1979.
Houben-Weyl: "Methoden der Organischen Chemie", 44th Ed., vol. IX, 1955, p. 215.
L. Skattebol et al, Journal of Organic Chemistry, vol. 32, Oct. 1967, pp. 3111-3114, Easton, USA, "Reactions of Sulfides with T-Butyl Hypochlorite".
C. Walling and M. J. Mintz, J. Org. Chem., vol. 32, pp. 1286-1289 (1967).
A. E. Wood et al., JACS, vol. 50, pp. 1226-1228 (1928).

Primary Examiner—Joseph L. Schofer
Assistant Examiner—F. M. Teskin
Attorney, Agent, or Firm—Stevens, Davis, Miller & Mosher

[57] ABSTRACT

Process for the preparation of pharmacologically active compounds containing a sulfoxide group by oxidation of a thioether with hypochlorite in an alkaline medium at a pH higher than 10 and at a temperature comprised between 0° and 40° C.

8 Claims, No Drawings

PROCESS FOR THE PREPARATION OF PHARMACOLOGICALLY ACTIVE COMPOUNDS CONTAINING A SULFOXIDE GROUP

The present invention relates to a process for the preparation of pharmacologically active compounds containing a sulfoxide group. It is known that the oxidation of thioethers to sulfoxides always takes place together with the formation of a certain amount of the corresponding sulfones. The amount of sulfone varies by varying the substream, the used reactants and the conditions under which the oxidation reaction is carried out. However, when drugs for human usage have to be prepared, event little amounts of sulfones represent an undesired by-product and their removal, by several fractional crystallizations, involves the loss of high amounts of pharmacologically active products (sulfoxides).

It is known that hypochlorite, in mild alkaline conditions, oxidizes thioethers to sulfones (A. E. Wood et al., J. Am. Chem. Soc., 50, (1928), 1226–8).

It has been now surprisingly found that thioethers may be oxidized to sulfoxides by an easy, practical, cheap and selective process using hypochlorite in an alkaline medium.

Thus, object of the present invention is a selective process for the oxidation of thioethers to sulfoxides consisting of carrying out the oxidation reaction with hypochlorite at a pH higher than 10.

Among the pharmacologically active compounds which can be conveniently prepared by the process object of the present invention, there are Esproquin, Mesoridazine, Oxfendazole, Opromazine, Perphenazinesulfoxide, Sulfinpyrazone, Sulindac, Suloxifen and Tixanox [see "Merck Index, 10th Edition, 1983; "Index Nominum 1982"; "USAN and the USP Dictionary of Drug Names", M. C. Griffith Editor, The United States Pharmacopeial Convention Inc., Rockville (USA) 1981]. The foregoing pharmacologically active compounds are named by their common names. The corresponding chemical names are:

Esproquine=approved international common name (AICN) of the compound 2-[3-(ethylsulfinyl)-propyl]-1,2,3,4,-tetrahydroisoquinoline Mesoridazine=AICN of compound 2-methylsulfinyl-10-[2-(1-methyl-2-piperidinyl)-ethyl]-phenothiazine Oxfendazole=AICN of compound 5-phenylsulfinyl-1H-benzimidazole-2-methylcarbamate Perphenazinesulfoxide=proposed common name of compound 4-[3-(2-chlorophenothiazin-10-yl)-propyl]-1-piperazineethanol Sulfinpyrazone=AICN of compound 1,2-diphenyl-4-[2-(phenylsulfinyl)-ethyl]-3,5-pyrazolidinedione Sulindac=AICN of compound 5-fluoro-2-methyl-1-[(4-methylsulfinyl)-phenyl]-methylene-1H-indene-3-acetic acid Suloxifene=AICN of compound N-(2-diethylaminoethyl)-S,S-diphenylsulfoximide Tixanox=AICN of compound 7-methylsulfinyl-9-oxoxanthene-2-carboxylic acid Opromazine or Oxychlorpromazine=proposed common name of compound 3-chloro-10-dimethylaminopropyl-phenothiazine-5-oxide.

The sulfoxide-derivatives of certain penicillins are useful starting products for the preparation of cephalosporins [Chemical Reviews, 76, 113–115, (1976)].

The process of the present invention, besides being particularly selective, allows the use of an oxidizing agent cheaper than most of the generally used oxidizing agents, such as peracids and peroxycompounds. Hydrogen peroxide only can compete, from an economical point of view, with hypochlorite, but hydrogen peroxide has the disadvantage, like all the peroxycompounds, to cause, in some cases, explosive side reactions.

This is particularly true when the substrate to be oxidized contains other functional groups which may interact; a specific example is the carboxylic group which may interact to form peracids.

Examples of compounds containing the carboxylic group are Sulindac and Tixanox.

The process of the present invention is carried out in a suitable diluent, preferably water, by adding the hypochlorite to the thioether, or vice-versa, at a temperature comprised between 0° and 40° C.

Thioether and hypochlorite are preferably used in the molar ratio 1:1. Alkali metal hypochlorites such as sodium hypochlorite are suitable in the process of the invention.

When the process is performed at a pH comprised between 10 and 12, it is preferable to add slowly the hypochlorite to the thioether; on the contrary, when the process is performed at a pH higher than 12 it is also possible to add the thioether to the hypochlorite and the addition in this case may also be fast.

The alkaline medium may be aqueous sodium or potassium hydroxide or an aqueous solution of sodium or potassium carbonate.

The basicity of the hypochlorite solution may be sufficient depending on the substrate to be oxidized.

When the thioether is sparingly soluble or insoluble in water, the reaction diluent may be a mixture of water and an organic solvent admixable with water and inert to hypochlorite. Suitable solvents include methanol, ethanol and dioxane.

Furthermore, it has been found, and this is a further object of the present invention, that the oxidation of thioether to sulfoxide may also be suitably carried out in the presence of a dialkylsulfoxide, e.g. dimethylsulfoxide.

This is particularly useful whenever it is preferred to work at a pH comprised between 10 and 12 and/or whenever an excess of hypochlorite is used.

The amount of dialkylsulfoxide to be used is comprised between 3 and 20 mols for one mole of thioether.

The sulfoxide which forms by oxidizing the thioether is separated by normal procedures.

The process object of the present invention is very convenient because of its high selectivity.

The only result is the oxidation of the thioether group to the corresponding sulfoxide.

The formation of undesired sulfones is practically avoided.

Furthermore, the compound to be oxidized may contain other functional groups like carbon-carbon double bonds or carboxylic groups which do not interfere with the oxidation according to the present invention but which, under different reaction conditions and with different oxidizers, may form undesired by-products like epoxides or peroxyacids.

The process of present invention has been considered in particular in its application to the preparation of pharmacologically active compounds because of the high selectivity requested in such applications and because of the fact that very often pharmacologically active compounds contain various functional groups.

However, it is evident that the preparation of other sulfoxides by operating according to the described process is comprised in the scope of the present invention.

The following examples are given to better illustrate the invention without limiting it.

Examples 1 to 5 concern the preparation of the compound known as Sulindac of formula

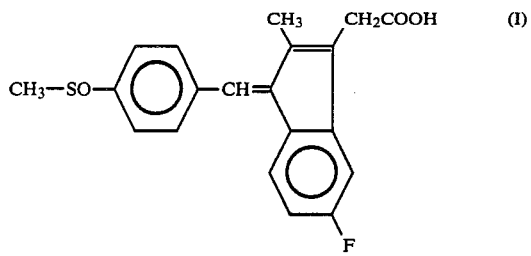

Sulindac was selected because of the fact that it contains various functional groups such as double bonds and a carboxylic group, in order to show the high selectivity of the process object of the invention.

The work-up of the reaction mixture, after the oxidation reaction, allows to obtain Sulindac in high yields and in a very pure form.

EXAMPLE 1

Preparation of 5-fluoro-2-methyl-1-[(4-methylsulfinyl)-phenyl]-methylene-1H-indene-3-acetic acid (I)

10 g (0.02937 mol) of 5-fluoro-2-methyl-1-[(4-methylthio)-phenyl]methylene-1H-indene-3-acetic acid (II), suspended in 200 g of water, are treated with 30% aqueous potassium hydroxide in such an amount to afford a solution having a pH comprised between 12 and 13.

36.44 g (titre 6%; 0.02937 mol) of sodium hypochlorite are then added at room temperature and within 30 minutes.

After having completed the addition, the mixture is kept under stirring for 30 minutes and thereafter it is poured dropwise into 60 g of 10% hydrochloric acid.

The precipitate (compound I), after having been filtered, washed with water and dried in oven at 60° C. in vacuo, weighs 10.2 g; its purity is higher than 99%.

EXAMPLE 2

To the mixture consisting of water (190 g), dimethylsulfoxide (10 g; 0.128 mol) and compound II (10 g; 0.02937 mol) are slowly added 11.79 g of 30% aqueous potassium hydroxide.

To the thus obtained solution (pH 13) 40.98 g (titre 5.49%; 0.03022 mol) of sodium hypochlorite are added dropwise.

After having completed the addition, the solution is kept under stirring for 30 minutes and thereafter it is poured dropwise into 60 g of 10% hydrochloric acid.

The precipitate is filtered, washed with water and dried in oven at 60° C. in vacuo to afford 10.2 g of compound I with a purity higher than 99%.

EXAMPLE 3

The solution obtained by mixing water (200 g), potassium carbonate (10 g; 0.07235 mol) and compound II (10 g; 0.02937 mol) is additioned with sodium hypochlorite (36.44 g; titre 6.0%; 0.02937 mol), at room temperature and within 30 minutes. After having completed the addition, the solution is kept stirring for 30 minutes and then it is poured dropwise into 60 g of 10% hydrochloric acid.

The obtained precipitate is filtered, washed with water and dried in oven at 60° C. in vacuo; 10 g of compound I are obtained, showing a purity higher than 99%.

EXAMPLE 4

The solution obtained by mixing water (190 g), dimethylsulfoxide (10 g; 0.128 mol), potassium carbonate (10 g; 0.07235 mol) and compound II (10 g; 0.02937 mol) is additioned with sodium hypochlorite (24.27 g; titre 10.81%; 0.03524 mol) at room temperature and within 30 minutes.

After having completed the addition the solution is kept under stirring for 30 minutes, then it is poured dropwise into 60 g of 10% hydrochloric acid. The thus obtained precipitate is filtered, washed with water and dried in oven at 60° C. in vacuo to give 10.26 g of compound I with a purity higher than 99%.

EXAMPLE 5

10 g (0.02937 mol) of compound II are added at room temperature and within 10 minutes to the solution obtained by adding 4.65 g of potassium hydroxide and 36.44 g (titre 6%; 0.02937 mol) of sodium hypochlorite to 200 g of water.

The obtained solution (pH 13) is kept under stirring for 30 minutes and then is poured dropwise into 60 g of 10% hydrochloric acid.

The thus obtained precipitate is filtered, washed with water and dried in oven at 60° C. in vacuo to give 10.3 g of compound I, with a purity higher than 99%.

EXAMPLE 6

Preparation of methylsulphinyl-benzene (C$_6$H$_5$—SO—CH$_3$)

To a solution of methyl-phenyl-sulphide (6.2 g) in water (2 ml) and dioxane (98 ml), stirred at 20° C. (external bath), sodium hypochlorite (88.69 g, titre 4.19%, pH 12.5) is added in 30 minutes.

The reaction mixture is further stirred at 20° C. for 20 minutes. Thereafter, dioxane is evaporated at reduced pressure and the residue is diluted with water (50 ml) and extracted with dichloromethane (2×30 ml).

The combined organic extract is washed with water (30 ml) and dried on sodium sulphate.

Evaporation of the solvent at reduced pressure affords the desired product (6 g) having a purity higher than 99%.

EXAMPLE 7

Preparation of benzyl-phenyl-sulfoxide

To a solution of benzyl-phenylsulphide (0.5 g) in dioxane (20 g) and water (2.5 g), stirred at 20° C., sodium hypochlorite (6.16 g, titre 4.3%) is added in 30 minutes.

The reaction mixtures is stirred at the same temperature for further 20 minutes, then it is worked up according to the procedure of Example 6.

The desired product (0.5 g) is obtained with a purity higher than 99%.

EXAMPLE 8

By operating according to the procedure described in Example 7, ethyl-phenyl-sulphide (0.5 g) was oxidized to ethylsulphinyl-benzene (yield 93%, purity higher than 99%).

What I claim is:

1. A process for the preparation selectively of compounds containing a sulfoxide group while substantially avoiding undesired sulfones consisting of oxidizing the corresponding thioethers with an alkali metal hypochlorite in an alkaline medium having a pH higher than 10 and at a temperature between 0° and 40° C.

2. A process according to claim 1, characterized in that the compound to be prepared is selected from the group consisting of Esproquin, Mesoridazine, Oxfendazole, Opromazine, Perphenazinesulfoxide, Sulfinpyrazone, Sulindac, Suloxifen and Tixanox.

3. A process according to claim 1, characterized in that the reaction is carried out in the presence of a dialkylsulfoxide.

4. A process according to claim 3, characterized in that 3–20 mols of dialkylsulfoxide are used for one mol of thioether.

5. A process according to claim 4, characterized in that the dialkylsulfoxide is dimethylsulfoxide.

6. A process according to claim 1, characterized in that the hypochlorite is sodium hypochlorite.

7. A process according to claim 1, characterized in that the alkaline medium is aqueous sodium or potassium hydroxide or an aqueous solution of sodium or potassium carbonate.

8. A process according to claim 1, characterized in that the reaction medium consists of a mixture of water and an organic solvent admixable with water but inert to hypochlorite.

* * * * *